United States Patent [19]

Fenrick

[11] 4,437,337
[45] Mar. 20, 1984

[54] VISCOELASTOMETER

[75] Inventor: Walter J. Fenrick, Medicine Hat, Canada

[73] Assignee: Her Majesty the Queen in right of Canada, as represented by the Minister of National Defence, Canada

[21] Appl. No.: 309,164

[22] Filed: Oct. 6, 1981

[30] Foreign Application Priority Data

Aug. 31, 1981 [CA] Canada .................................. 384906

[51] Int. Cl.$^3$ ...................... G01N 11/10; G01N 13/02
[52] U.S. Cl. ........................................ 73/54; 73/64.4; 73/169
[58] Field of Search ........................... 73/64.4, 54, 169

[56] References Cited

U.S. PATENT DOCUMENTS

| 1,960,224 | 5/1934 | Schoenberg | 73/64.4 |
| 3,043,131 | 7/1962 | Heneage | 73/64.4 |
| 3,415,109 | 12/1968 | Sucker et al. | 73/64.4 |
| 3,463,014 | 8/1969 | Katz et al. | 73/169 X |
| 3,780,569 | 12/1973 | Graham | 73/64.4 |

FOREIGN PATENT DOCUMENTS 367367 3/1973 U.S.S.R. ................ 73/64.4

OTHER PUBLICATIONS

Rosano, H. L. et al., *Determination of the Critical Surface Tension Using an Automatic Wetting Balance*, In Journ. of Coll. and Interface Sci., 36(3): pp. 298–307, Jul. 1971.
Kee, D. et al., *New Method for the Determination of Yield Stress*, In Journ. of Text. Stud. 10, pp. 281–288, Sep. 17, 1979.

*Primary Examiner*—Gerald Goldberg
*Assistant Examiner*—Joseph W. Roskos
*Attorney, Agent, or Firm*—Kerkam, Stowell, Kondracki & Clarke

[57] ABSTRACT

A viscoelastometer for measuring and displaying a viscoelastic effect in a liquid such as water, oils, paints, blood or thickened liquids or suspensions including types commonly used as foods or pharmaceuticals as a reproducible force time signature. The viscoelastometer comprises a rigid member suspended from the free end of a resilient, deflectable cantilever which extends from a rigid support, a liquid sample cup associated with a pneumatic cylinder for moving the sample cup at a selected rate between an upper position at which the rigid member is immersed to a predetermined depth in the liquid and a lower position at or before which occurs relaxation and separation of a filament of the liquid which forms between the rigid member and the surface of the liquid during downward movement of the sample cup, strain gauges associated with a portion of the cantilever intermediate the rigid member and the rigid support, and a display associated with the strain guages to display a quantitatively reproducible force time signature representative of the viscosity and elasticity of the liquid as a function of the sensed strain imparted to the cantilever as the sample cup is moved between the upper and lower positions.

8 Claims, 7 Drawing Figures

VISCOELASTOMETER

FIELD OF THE INVENTION

The present invention relates to a viscoelastometer for measuring the rheological properties of a liquid. The viscoelastometer provides quantitatively reproducible force time signatures unique to a given liquid which can be related to the viscosity and elasticity of that liquid.

DESCRIPTION OF THE PRIOR ART

The viscosity of a liquid is typically determined by rotating an object in a liquid sample and measuring the counter-rotational force applied to the object by the liquid. Such devices, of which the Brookfield and Stormer viscosimeters are typical, provide a measurement of viscosity normally expressed in poise for a given rotational speed (rpm) and temperature.

In order to visually compare the elasticity of various liquids it has been customary for laboratory personnel to dip the pointed end of a pencil into a liquid sample and then withdraw it from the liquid at a rate of approximately 12 to 15 centimeters per second. If the liquid was thick and sticky a filament of the material would form, stretching from the pointed end of the pencil down to the surface of the liquid, and then relax and separate over a length of time dependent upon the elasticity of the liquid. The test is only useful for rough, comparative purposes, and even then the usefulness of the observations are highly dependent upon the skill and experience of the individual performing the test.

SUMMARY OF THE INVENTION

The viscoelastometer of the present invention provides quantitatively reproducible force time signatures unique to a given liquid which can be related to the viscosity and elasticity of that liquid.

In one particular aspect the present invention provides apparatus for measuring the rheological properties of a liquid, comprising a resilient, deflectable cantilever extending from a rigid support, a rigid member extending downwardly from the cantilever, a sample cup adapted to contain a liquid sample, means for moving the sample cup at a selected rate between an upper position at which the rigid member is immersed to a predetermined depth in a liquid contained in the sample cup and a lower position at or before which occurs relaxation and separation of a filament of the liquid which forms between the rigid member and the surface of the liquid during movement of the sample cup from the upper position toward the lower position, strain sensing means associated with a portion of the cantilever intermediate the rigid member and the rigid support, and display means associated with the strain sensing means for displaying the rheological properties of the liquid as a function of the sensed strain imparted to the cantilever by the liquid as the sample cup is moved between the upper and lower positions.

In another particular aspect the present invention provides apparatus for measuring the rheological properties of a liquid, comprising a resilient, deflectable cantilever extending substantially horizontally from a vertically adjustable rigid support, a rigid member pivotally suspended from the cantilever, a sample cup adapted to contain a liquid sample, pneumatic cylinder means for moving the sample cup at a selected rate between an upper position at which the rigid member is immersed to a predetermined depth in a liquid contained in the sample cup and a lower position at or before which occurs relaxation and separation of a filament of the liquid which forms between the rigid member and the surface of the liquid during movement of the sample cup from the upper position toward the lower position, strain sensing means associated with a portion of the cantilever intermediate the rigid member and the rigid support, an oscilloscope associated with the strain sensing means for displaying the rheological properties of the liquid as a function of the sensed strain imparted to the cantilever as the sample cup is moved between the upper and lower positions, and means to minimize or eliminate vibrational excitation of the cantilever caused by operation of the pneumatic cylinder means for moving the sample cup at a selected rate between the upper and lower positions or by sources of vibration external to the apparatus.

In the Drawings

DETAILED DESCRIPTION OF THE INVENTION

Figure 1:
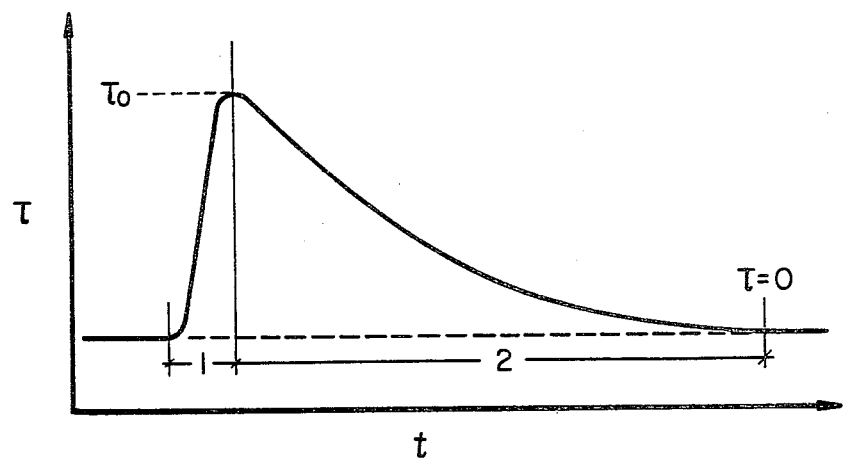
FIG. 1 is a diagrammatic illustration of a force time signature exemplary of the type produced by a viscoelastometer according to the present invvention.

Referring to the exemplary force time signature illustrated in FIG. 1, the first part (1) of the signature is due to stretching of a filament of the liquid while the second part (2) is due to subsequent relaxation of the filament.

The part of the signature which is of paramount interest is the second part since, ignoring the fact that there is some viscous flow within the filament after it is stretched, the second part of the signature is due to stress relaxation of the liquid molecules and is primarily a function of the elasticity of the fluid. For the case of a viscoelastic fluid analysed according to the Maxwell model, the stress relaxation can be defined by the equation:

$$\tau = \tau_0 e^{-t/\lambda} \tag{I}$$

where:
$\tau$ = stress;
t = time; and
$\lambda$ = relaxation time for the viscoelastic liquid.

The relaxation time can be equated to the viscosity of the liquid ($\eta_o$) and the shear modulus (G) by the equation:

$$\lambda = \eta_o/G \qquad (II)$$

Thus measurement of $\lambda$ for a series of liquids with substantially identical viscosities permits a quantitative comparison of differences in elasticity of the liquids.

Figure 2:
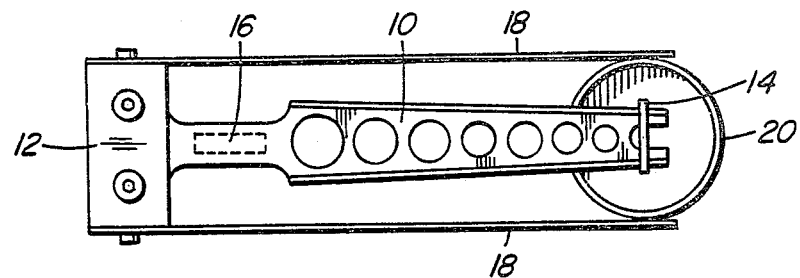
FIG. 2 is a top plan view of an embodiment of a cantilever assembly of a viscoelastometer according to the present invention.
Figure 3:
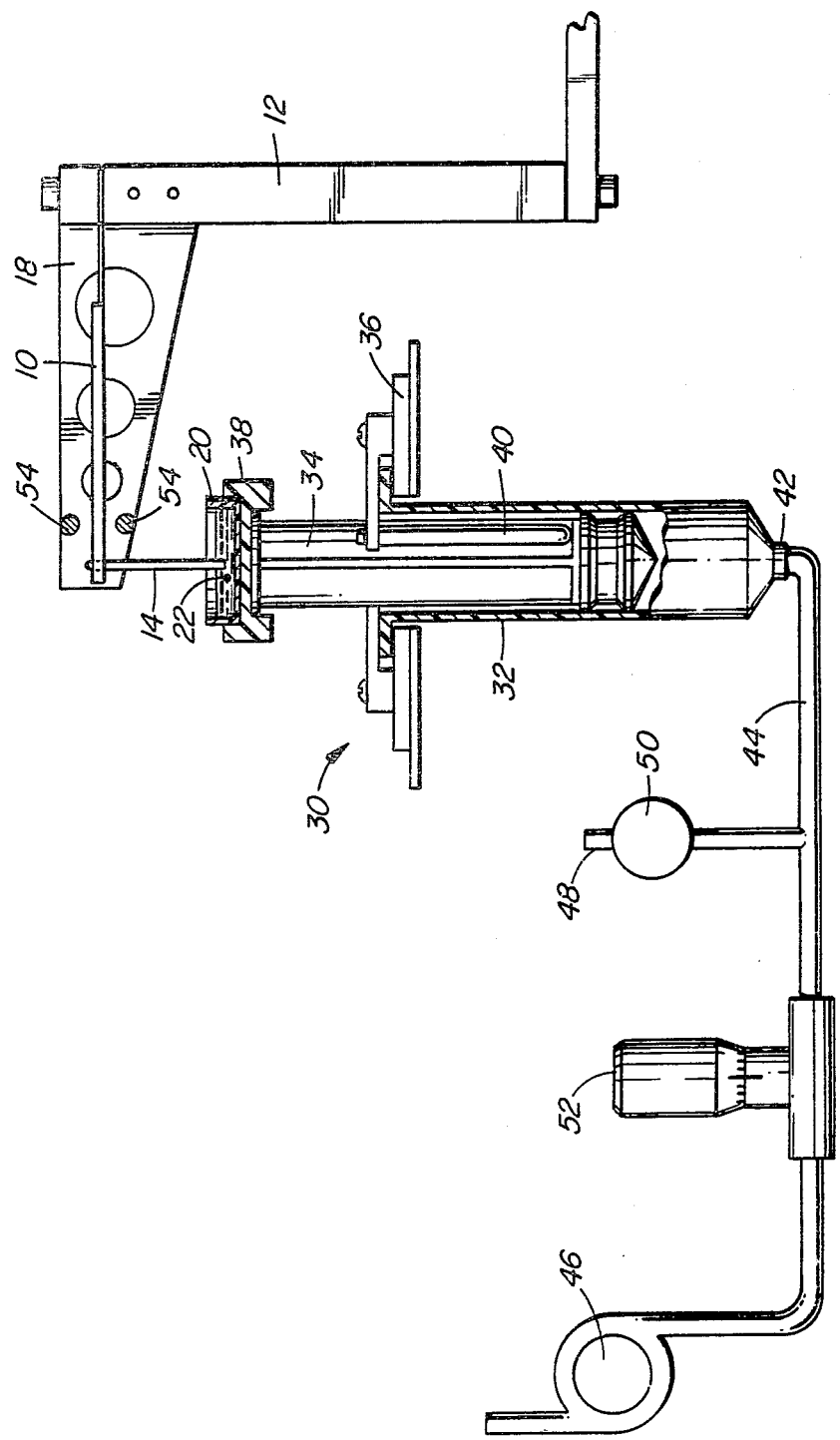
FIG. 3 is a side elevation view, partly in section, of an embodiment of a viscoelastometer according to the present invention.

Referring now to FIGS. 2 and 3, in which like parts are identically numbered, a resilient, deflectable cantilever 10 extends from a rigid, vertically adjustable support 12. A rigid member 14 is suspended from the free end of the cantilever 10. In the embodiment illustrated, as best seen from FIG. 2, the cantilever 10 includes a waisted section, on either side of which are mounted strain guages (not shown) electrically connected to form a typical half-bridge configuration for sensing strain in the area 16 of the cantilever 10. The strain guages typically are electrically connected to a signal amplifier and a display means such as an oscilloscope (also not shown) for displaying the sensed strain in the area 16.

An assembly 30, an embodiment of which is illustrated in FIG. 3, is provided for mounting a sample cup 20 and moving the sample cup at a selected rate between an upper position at which the rigid member 14 is immersed to a predetermined depth in a liquid sample 22 contained in the sample cup 20 and a lower position at or before which occurs relaxation and separation of the filament of the liquid which forms between the rigid member 14 and the surface of the liquid sample 22 during movement of the sample cup 20 from the upper position toward the lower position. The assembly 30 includes a conventional hypodermic syringe having a barrel 32 and a plunger 34. The barrel 32 is fixed in a support 36, and an adapter 38 is provided on the top of the plunger 34 to hold the sample cup 20. A stop member 40 is associated with the support 36 to limit upward movement of the plunger 34 in the barrel 32. The outlet 42 of the syringe is connected to a line 44 which communicates with a vacuum pump 46. A line 48, controllably communicating with the atmosphere by a valve 50, which for example can be selectively operated by means of a solenoid and associated switch and power supply (also not shown), joins line 44 intermediate the syringe outlet 42 and the vacuum pump 46. A flow volume control valve 52, for example a micrometer needle valve, is also provided in line 44 intermediate line 48 and the vacuum pump 46.

In operation of the viscoelastometer, the valve 50 is opened to prevent evacuation of that portion of the barrel 32 downstream of the plunger 34 by the vacuum pump 46. A liquid sample 22 is placed in the sample cup 20 and the plunger 34 is moved to the upper position dictated by the stop member 40. The support 12 is then adjusted vertically, as necessary, so that the rigid member 14 is immersed to the desired depth in the liquid sample 22 in the sample cup 20, nominally as shown in FIG. 3. Upon closing of the valve 50 the plunger 34 moves downwardly within cylinder 32 at a velocity governed by the volumetric rate of flow through the control valve 52 to a lower position, which at a maximum is when the plunger 34 bottoms in the barrel 32 or when the adapter 38 abuts the support 36. As the plunger moves between the upper and lower positions a filament of the liquid initially forms between the rigid member 14 and the surface of the liquid sample 22 and subsequently relaxes and separates as a function of the viscosity and elasticity of the liquid. The weight of the filament on the rigid member 14 strains the cantilever 10, and is sensed by the strain guages and in turn displayed by the oscilloscope as a curve similar to that of the first part (1) of the exemplary force time signature illustrated in FIG. 1. As the filament relaxes and separates, the strain in the cantilever 10 abates over a length of time dependent upon the viscosity and elasticity of the liquid, and is again sensed by the strain guages and in turn displayed by the oscilloscope as a curve similar to that of the second part (2) of the exemplary force time signature illustrated in FIG. 1.

In the particular embodiment constructed and tested, and generally illustrated in FIGS. 2 and 3, the cantilever 10 was made of 0.25 mm thick phosphor bronze, and the rigid member 14 was a T-shaped rod made by soldering together two lengths of 17 guage hypodermic needle and plugging the tip of the bore of the end portion intended for immersion in the liquid samples. The other end was pivotally suspended from the cantilever as best shown in FIG. 3. The assembly proved to be extremely sensitive, for which reason it proved desirable to ensure, to the extent possible, that the cantilever 10 be vibrationally isolated from sources of excitation other than the effect on the rigid member 14 of the test liquid. To this end, the support 12 ultimately employed, and which is only illustrated schematically in FIG. 3, was a UNERTL ® mirror mount positioned on a vibration isolation pad. The components and associated supports of the assembly 30, which are also only illustrated schematically in FIG. 3, were also positioned on vibration isolation pads.

While the particular embodiment illustrated in FIGS. 2 and 3 employed a T-shaped rod as the rigid member 14, other geometries such as a rectangular blade can readily be employed.

While the particular embodiment illustrated in FIG. 3 employed a hypodermic syringe as the means of moving the sample cup 20 between the upper and lower positions, it will be obvious to those skilled in the art that other means to accomplish the same end can readily be employed. By way of example only, the hypodermic syringe could readily be replaced by a double acting pneumatic cylinder.

Although not illustrated in FIG. 3, the environment of the viscoelastometer is preferably controlled, for example by placing the viscoelastometer in a thermostatically controlled housing so that the test liquid can be maintained at a desired predetermined temperature. Alternately, the test liquid temperature can be controlled by placing a suitable heating/cooling assembly such as a water jacket around the test liquid.

To protect the cantilever 10 from accidental damage, guards 18, one of which has been removed for clarity in FIG. 3, were mounted on support 12. Additionally, cantilever deflection stops 54, illustrated only in FIG. 3, were provided on one of the guards 18 to limit undue deflection of the cantilever 10. It was also discovered, during testing, that high frequency oscillations of the cantilever 10 caused by sources other than the test liquid could be significantly damped by provision of a small amount of silicone grease between the cantilever 10 and the upper cantilever deflection stop 54 without significantly affecting the shapes of the force time signatures indicative of the rheological properties.

FIGS. 4, 4a, 5 and 5a are oscilloscope tracings of actual force time signatures produced by a viscoelastometer according to the present invention. In the tracings each vertical division represents 0.1 volts and each horizontal division 0.1 seconds and were produced with a rigid member immersion depth of 0.25 cm and a constant plunger velocity, nominally in the range of 12 to 15 cm/sec.

Figure 4A:
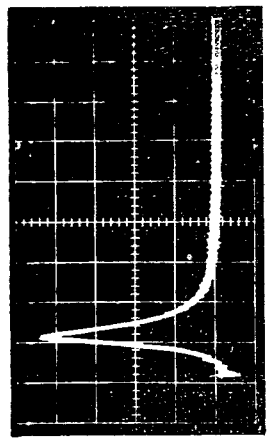
FIG. 4a is a superimposition of 20 separate force time signatures of SAE 50 motor oil produced under constant conditions by a viscoelastometer according to the present invention.
Figure 4:
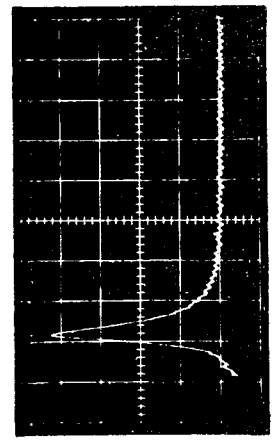
FIG. 4 is a force time signature of SAE 50 motor oil produced by a viscoelastometer according to the present invention.

FIG. 4 represents a single force time signature of SAE 50 motor oil, whereas FIG. 4a is a superimposition of 20 separate force time signatures of the same SAE 50 motor oil and illustrates the reproducibility of the force time signatures produced by the viscoelastometer.

Figure 5A:
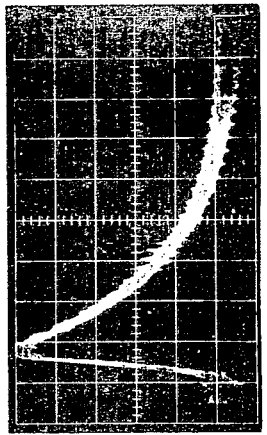
FIG. 5a is a superimposition of 20 separate force time signatures of Dowanol ® thickened with Rohm and Haas K125 polymer produced under constant conditions by a viscoelastometer according to the present invention.
Figure 5:
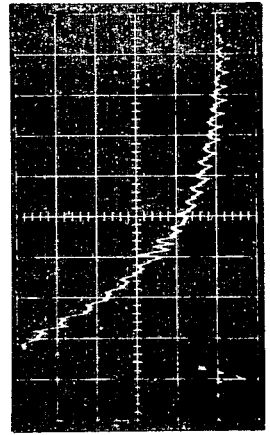
FIG. 5 is a force time signature of Dowanol ® thickened with Rohm and Haas K125 polymer produced by a viscoelastometer according to the present invention.

FIG. 5 represents a single force time signature of Dowanol ® thickened with Rohm and Haas K125 polymer, whereas FIG. 5a is a superimposition of 20 separate force time signatures of the same Dowanol ® thickened with Rohm and Haas K125 polymer and again illustrates the reproducibility despite the fact that the force time signatures were not entirely contained within the tracing. The force time signatures could be produced to appear entirely within the oscilloscope tracing boundaries by variation of the vertical and horizontal oscilloscope settings, but in FIGS. 5 and 5a the settings were maintained identical to those employed to produce the force time signatures of FIGS. 4 and 4a to permit direct size comparison of the force time signatures of SAE 50 motor oil and the thickened Dowanol ®.

The immersion depth of the rigid member 14 in the test liquid theoretically should not affect the relaxation time $\lambda$ since $\lambda$ is a function of viscosity and elasticity. The values for $\lambda$, with incrementally increasing immersion depths starting at point contact of the rigid member with the surface of the test liquid, using Dowanol ® DPM thickened with Rohm and Haas K125 polymer to a viscosity of 18.4 poise, are set out in the following table:

| Run No. | Immersion (cm) | $\lambda$ (sec) |
|---|---|---|
| 1 | 0.000 | 0.35 |
| 2 | 0.025 | 0.35 |
| 3 | 0.050 | 0.35 |
| 4 | 0.075 | 0.34 |
| 5 | 0.100 | 0.34 |
| 6 | 0.125 | 0.35 |
| 7 | 0.150 | 0.32 |
| 8 | 0.175 | 0.34 |
| 9 | 0.200 | 0.34 |

Average value of $\lambda$ 0.342 sec

The above table demonstrates that the relaxation time $\lambda$ is not a function of the immersion depth of the rigid member in the test liquid, and also again illustrates the reproducibility of the force time signatures produced by the viscoelastometer of the invention. Analysing this data according to the Maxwell model for a viscoelastic liquid (e.g. equations I and II), with an average relaxation time of 0.34 seconds and a viscosity of 18.4 poise, a shear modulus of 51.4 g/cm.s is obtained thereby demonstrating that the viscoelastometer of the invention provides a reliable means of measuring rheological properties of liquids.

Various modifications and variations falling within the true broad spirit and scope of the invention will be readily apparent to those skilled in the art.

I claim:

1. Apparatus for measuring and displaying a viscoelastic effect in a liquid as a reproducible force/time signature which can be related to the viscosity and elasticity of the liquid, said apparatus comprising a resilient, deflectable cantilever extending from a rigid support, a rigid rod extending downwardly from the cantilever, a sample cup adapted to contain a liquid sample, means for moving the sample cup at a selected rate between an upper position at which the rigid rod is immersed to a predetermined depth in a liquid contained in the sample cup and a lower position at or before which occurs relaxation and separation of a filament of the liquid which forms between the rigid rod and the surface of the liquid during movement of the sample cup from the upper position toward the lower position, strain sensing means associated with a portion of the cantilever intermediate the rigid rod and the rigid support for sensing the strain which occurs during the formation and subsequent relaxation and separation of the filament, and display means associated with the strain sensing means for displaying the sensed strain as a function of time to provide a reproducible force/time signature which can be related to the viscosity and elasticity of the liquid.

2. Apparatus according to claim 1, wherein the rigid support is vertically adjustable and the cantilever extends substantially horizontally from the rigid support.

3. Apparatus according to claim 1, wherein the rod is pivotally suspended from the cantilever.

4. Apparatus according to claim 1, wherein the means for moving the sample cup at a selected rate between the upper and lower positions is a pneumatic cylinder.

5. Apparatus according to claim 4, wherein the pneumatic cylinder is double acting.

6. Apparatus according to claim 1, wherein the display means is an oscilloscope.

7. Apparatus according to claim 1, including means to minimize or eliminate vibrational excitation of the cantilever caused by operation of the means for moving the sample cup at a selected rate between the upper and lower positions or by sources of vibration external to the apparatus.

8. Apparatus for measuring and displaying a viscoelastic effect in a liquid as a reproducible force/time signature which can be related to the viscosity and elasticity of the liquid, said apparatus comprising a resilient, deflectable cantilever extending substantially horizontally from a vertically adjustable rigid suport, a rigid rod pivotally suspended from the cantilever, a sample cup adapted to contain a liquid sample, pneumatic cylinder means for moving the sample cup at a selected rate between an upper position at which the rigid rod is immersed to a predetermined depth in a liquid contained in the sample cup and a lower position at or before which occurs relaxation and separation of a filament of the liquid which forms between the rigid rod and the surface of the liquid during movement of the sample cup from the upper position toward the lower position, strain sensing means associated with a portion of the cantilever intermediate the rigid rod and the rigid support for sensing the strain which occurs during the formation and subsequent relaxation and separation of the filament, an oscilloscope associated with the strain sensing means for displaying the sensed strain as a function of time to provide a reproducible force/time signature which can be related to the viscosity and elasticity of the liquid, and means to minimize or eliminate vibrational excitation of the cantilever caused by operation of the pneumatic cylinder means for moving the sample cup at a selected rate between the upper and lower positions or by sources of vibration external to the apparatus.

* * * * *